United States Patent [19]
Wilson et al.

[11] Patent Number: 5,792,084
[45] Date of Patent: Aug. 11, 1998

[54] KNEE BRACE HAVING AN INFLATABLE PAD CIRCUMSCRIBING THE PATELLA

[75] Inventors: Franklin D. Wilson, Carmel, Ind.; Charles A. Bastyr, San Diego, Calif.; Richard E. Gildersleeve, Escondido, Calif.; James M. Verespej, Vista, Calif.

[73] Assignee: Smith & Nephew, Inc., Memphis, Tenn.

[21] Appl. No.: 873,620

[22] Filed: Jun. 12, 1997

Related U.S. Application Data

[63] Continuation of Ser. No. 388,956, Feb. 15, 1995, abandoned, which is a continuation-in-part of Ser. No. 104,184, Aug. 10, 1993, Pat. No. 5,415,625, which is a continuation-in-part of Ser. No. 191,410, Feb. 3, 1994, Pat. No. 5,458,565, which is a continuation-in-part of Ser. No. 199,091, Feb. 22, 1994, abandoned, which is a continuation-in-part of Ser. No. 246,972, May 19, 1994, Pat. No. 5,527,268, which is a continuation-in-part of Ser. No. 251,858, May 31, 1994, Pat. No. 5,520,622.

[51] Int. Cl.⁶ ............................................. A61F 5/00
[52] U.S. Cl. ...................................... 602/13; 602/26
[58] Field of Search ............................. 602/5, 13, 23, 602/26, 61–63

[56] References Cited

U.S. PATENT DOCUMENTS

| | | |
|---|---|---|
| 4,201,203 | 5/1980 | Applegate . |
| 4,287,885 | 9/1981 | Applegate . |
| 4,378,009 | 3/1983 | Rowley et al. . |
| 4,872,448 | 10/1989 | Johnson, Jr. . |
| 4,938,207 | 7/1990 | Vargo . |
| 5,113,599 | 5/1992 | Cohen et al. . |
| 5,334,135 | 8/1994 | Grim et al. . |
| 5,378,224 | 1/1995 | Billotti . |
| 5,383,843 | 1/1995 | Watson et al. . |
| 5,385,538 | 1/1995 | Mann . |
| 5,451,201 | 9/1995 | Prengler . |

FOREIGN PATENT DOCUMENTS

| | | |
|---|---|---|
| 0492328 | 7/1992 | European Pat. Off. . |
| 2607384 | 12/1986 | France . |

*Primary Examiner*—Linda C. Dvorak
*Attorney, Agent, or Firm*—Brown, Martin, Haller & McClain

[57] ABSTRACT

A knee brace is provided that is mountable over the knee joint of a user. The brace has a compliant sleeve and a compliant cover overlying an anterior portion of the sleeve. The sleeve and cover preferably have corresponding anterior openings aligned to receive the patella when the brace is mounted over the knee joint. The sleeve and cover are joined around the perimeter of the cover to form a pocket therebetween enclosing an inflatable pad having a medial chamber and a lateral chamber in fluid isolation from each other. The chambers are provided with associated pumps and valves, rendering them selectively inflatable or deflatable. In operation, the brace is positioned over the knee joint such that the pad circumscribes a portion of the patella and one or both of the chambers are inflated as desired to stabilize the patella.

18 Claims, 3 Drawing Sheets

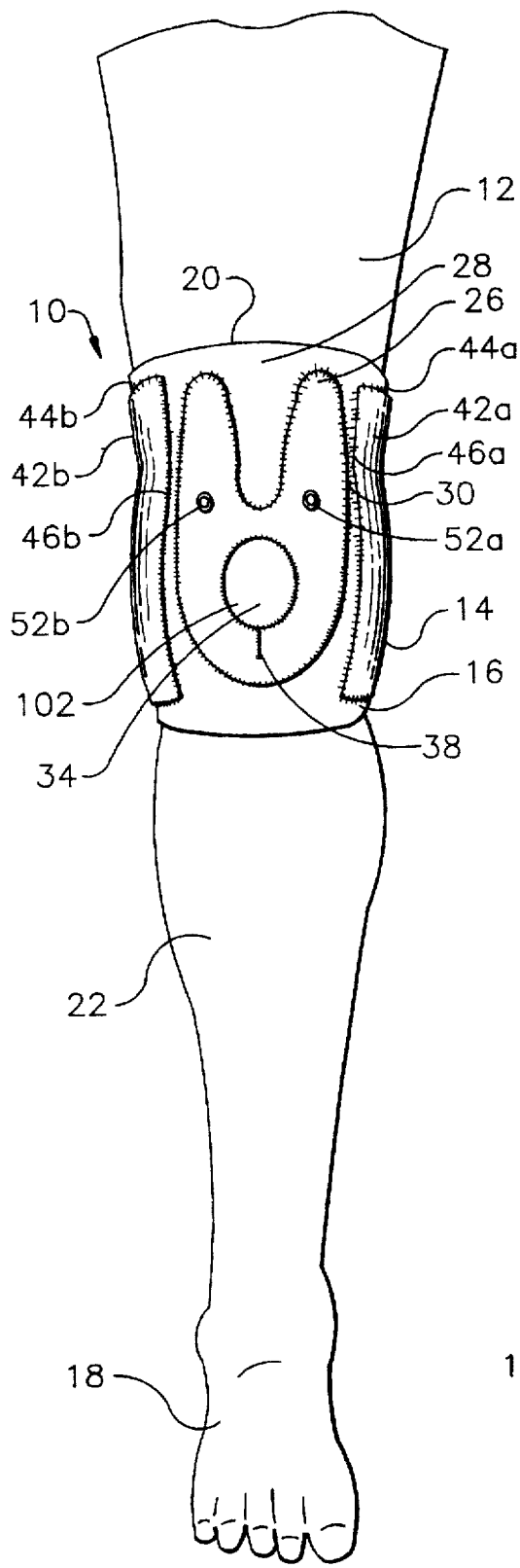
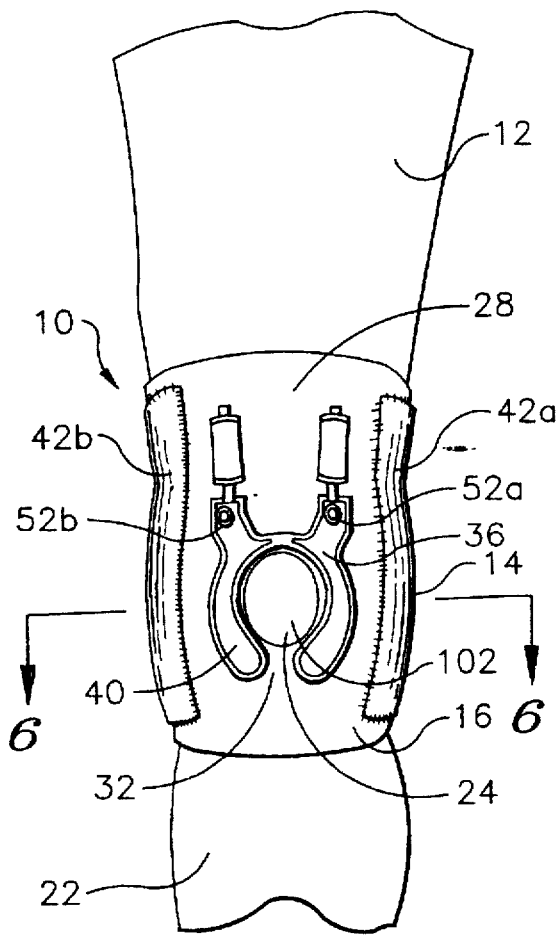
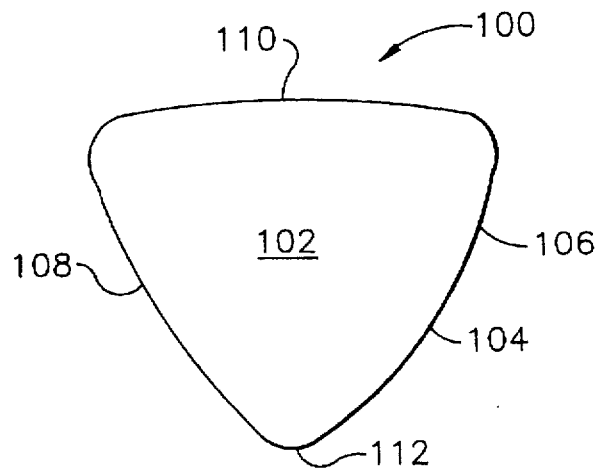

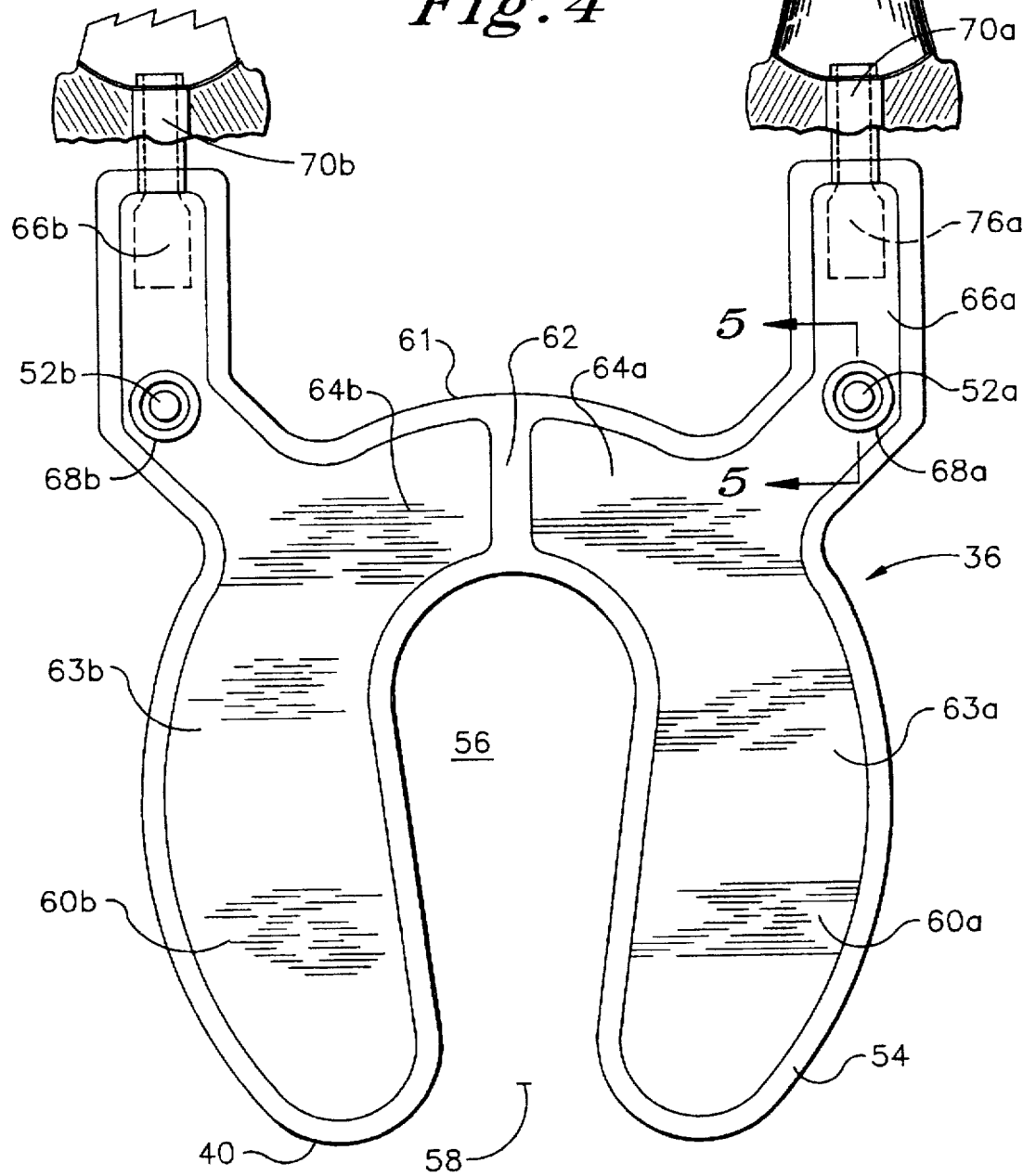

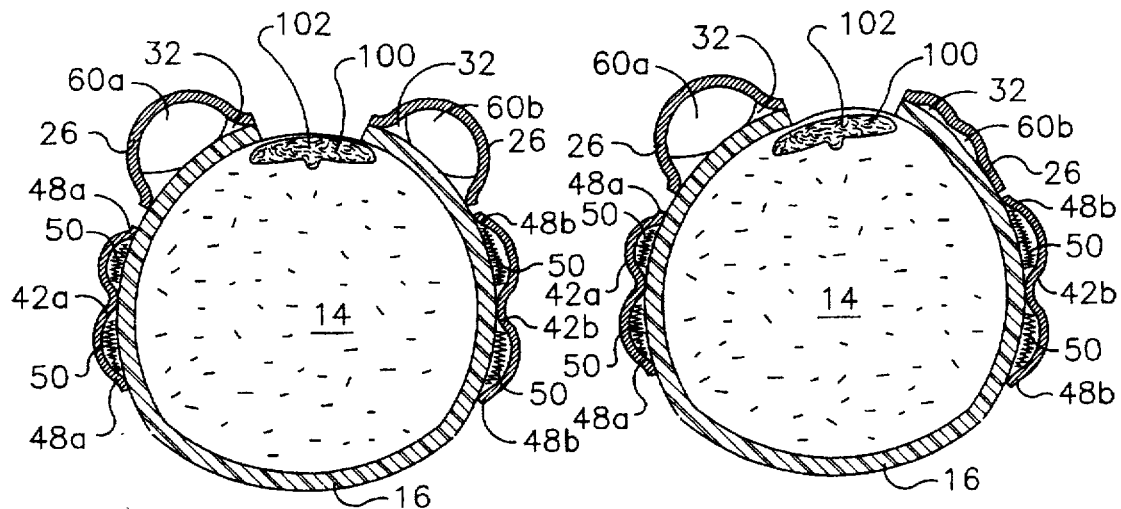
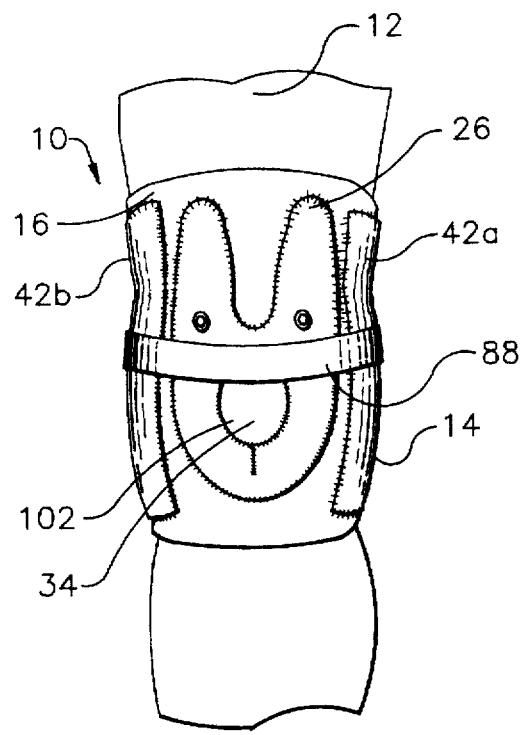
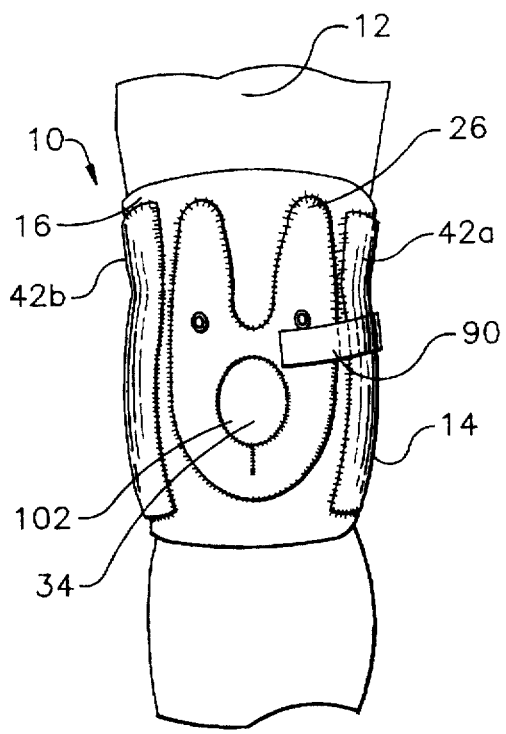

KNEE BRACE HAVING AN INFLATABLE PAD CIRCUMSCRIBING THE PATELLA

This is a continuation of application Ser. No. 08/388,956, filed Feb. 15, 1995, now abandoned which in turn is a continuation-in-part of application Ser. No. 08/104,184, filed Aug. 10, 1993, now U.S. Pat. No. 5,415,625, which is a continuation-in-part of application Ser. No. 08/191,410, filed Feb. 3, 1994, now U.S. Pat. No. 5,458,565, which is a continuation-in-part of application Ser. No. 08/199,091, filed Feb. 22, 1994, now abandoned, which is a continuation-in-part of application Ser. No. 08/246,972, filed May 19, 1994, now U.S. Pat. No. 5,527,268, which is a continuation-in-part of application Ser. No. 08/251,858, filed May 31, 1994, now U.S. Pat. No. 5,520,622.

TECHNICAL FIELD

The present invention relates generally to orthopedic braces, and particularly to an orthopedic brace containing a pad that applies a force against the knee of a user for stabilizing the knee. More particularly, though not exclusively, the present invention relates to such an orthopedic brace, wherein the pad is inflatable to selectively adjust the degree and direction of force against the patella of a user thereby maintaining the patella in a biomechanically correct position.

BACKGROUND OF THE INVENTION

It is recognized that many soft tissue conditions or injuries relating to the knee joint result from patellar dislocation. Consequently, a number of orthopedic knee braces have the primary function of isolating and stabilizing the position of the patella. For example, U.S. Pat. No. 4,370,978 discloses a knee brace having an elastic sleeve with a patellar opening. A pair of resilient pads are sewn to the inside of the sleeve to engage the medial and lateral sides of the patella and apply opposing balanced forces thereto when the brace is positioned on the leg of a user.

U.S. Pat. No. 4,201,203 discloses a knee brace having an elastic sleeve having a selectively fixed patellar opening to receive and tightly embrace various sized patellas. A single resilient pad configured to engage the sides of the patella is displacably affixed to the inside of the sleeve. The pads, in conjunction with a plurality of vertically-aligned stiffened stays incorporated into the sleeve, apply balanced opposing forces to the sides of the patella, thereby restricting movement of the patella.

U.S. Pat. No. 4,938,207 discloses a knee brace that applies variable support to the patella as a function of the position of the leg during dynamic exercise thereof. The knee brace has a system of inflatable chambers including four relatively small side chambers, two of which are configured to engage the medial side of the patellar circumference and two of which are configured to engage the lateral side of the patellar circumference. Each side chamber is in fluid isolation from the other, but is in fluid communication with a considerably larger remote chamber that is positioned against the thigh or calf away from engagement with the patella. The remote chamber serves as a fluid reservoir for its respective side chamber and each remote chamber is provided with a valve that enables selective addition of fluid to or withdrawal of fluid therefrom.

When a leg having the brace of U.S. Pat. No. 4,938,207 mounted thereon is flexed at the knee joint, the thigh or calf compresses the remote chambers, thereby transferring a large volume of fluid into the respective side chambers. The infusion of fluid into the relatively small side chambers substantially increases the fluid pressure therein and correspondingly increases the force load they apply to the medial and lateral sides of the patella. Consequently, medial and lateral support for the patella is markedly increased when the leg is flexed. Conversely, when the leg is extended at the knee joint, the thigh or calf decompresses the remote chambers, thereby returning the fluid from the side chambers back to their respective remote chambers. Consequently, medial and lateral support for the patella is markedly decreased when the leg is extended.

U.S. Pat. No. 4,378,009 discloses a knee brace having a single inflatable pneumatic pad in the shape of an elongated tube. The pad is selectively configured about the knee joint to circumscribe the entire patella and provide balanced compression forces thereto.

U.S. Pat. No. 4,872,448 likewise discloses a knee brace employing a single inflatable pneumatic pad to restrict the movement of the patella. The pneumatic pad, however, has a slotted longitudinal opening formed therein that fits over the patella. Consequently, the pad engages only the medial and lateral sides of the patella, applying balanced opposing compression forces thereto. The pad permits distal and proximal vertical dislocation of the patella along the path of the longitudinal opening, while restricting medial and lateral horizontal dislocation of the patella.

Despite the existence of braces in the prior art designed to stabilize the patella, a need continues for improved knee braces that more effectively stabilize the patella. Accordingly, it is an object of the present invention to provide a knee brace that satisfies this need. More particularly, it is an object of the present invention to provide a knee brace that resists undesirable patellar dislocation. It is another object of the present invention to provide a knee brace that biases and maintains the patella in a biomechanically correct position. It is yet another object of the present invention to provide such a knee brace, wherein the degree of bias is simply, effectively and selectively adjustable by the user. It is still another object of the present invention to provide a knee brace that is comfortable for the user. It is a further object of the present invention to provide a knee brace that does not overly restrict the mobility of the user. These objects and others are achieved by the invention described hereafter.

SUMMARY OF THE INVENTION

The present invention is a knee brace positionable on the knee joint of a user to resist dislocation of the patella from a desired position. The knee brace can also be used to selectively reposition and retain the patella in a biomechanically corrected position. The brace comprises a compliant sleeve formed from a relatively elastic material that is sized to enclose substantially the entire knee joint when the brace is mounted thereon. An anterior opening is optionally provided through the anterior face of the sleeve to circumscribe the patella and expose a portion of the patellar face.

The brace further comprises an anterior cover overlying a portion of the anterior face of the sleeve. The anterior cover is likewise optionally provided with an anterior opening corresponding to the anterior opening of the sleeve which avoids covering the exposed portion of the patellar face. The anterior cover may be formed from the same elastic material as the sleeve, but is preferably formed from a relatively less elastic material. The anterior cover is fixedly attached along its perimeter to the underlying anterior face of the sleeve, thereby creating a pocket between the sleeve and cover. The pocket encloses and secures a pad in a prescribed position on the sleeve that circumscribes substantially all but a lower portion of the patella, and correspondingly all but a lower portion of the anterior openings in the sleeve and anterior-cover.

The pad is a divided hollow bladder, enclosing a pair of arcuate-shaped chambers maintained in fluid isolation from each other. The chambers are substantially symmetrical, each having an elongated longitudinal segment in opposing, substantially corresponding alignment with the longitudinal axis of the sleeve. Each chamber also has a shortened transverse segment at the upper end of the longitudinal segment that curves inwardly toward the transverse segment of the opposing chamber in substantially transverse alignment with the longitudinal axis of the sleeve. The two chambers in combination define the configuration of the pad as an open loop substantially corresponding to, and circumscribing, the entire perimeter of the patella excluding, however, the inferior patellar apex. Accordingly, the pad has a substantially closed upper end and a substantially open lower end. The upper end, along with the medial and lateral sides of the pad, circumscribe the perimeter of a central opening in the pad, while a lower opening is provided at the lower end of the pad that adjoins the central opening.

The chambers are provided with one or more selectively resealable valves and pumps, enabling selective fluid communication between the interior and exterior of the chambers for separately adding fluid into each chamber or withdrawing fluid from each chamber. The brace may also be also provided with one or more straps, wherein each strap has two ends selectively connectable to the sleeve so that the strap can be adjustably disposed along the sleeve in a circumferential or longitudinal direction.

To operate the brace, the sleeve is placed over the knee joint of the user with the chambers at least partially deflated and the strap ends, if one or more straps are provided, free or loosely attached to the sleeve. The pad is aligned to circumscribe substantially all but the inferior apex of the patella, while the anterior openings of the sleeve and cover, if provided, are positioned over the patella with the patella exposed therethrough. The brace is rendered operable by inflating one or both of the chambers with a selected fluid, wherein the fluid is displaced into the chambers by means of the one or more release valves and pumps provided in association with the chambers.

As each chamber inflates and expands, the preferably relatively inelastic anterior cover directs the expansion of the chamber in the direction of the patella causing the chamber to radially impinge against the circumference of the patella engaged thereby. If it is desired to securely retain the patella in its inherently natural position, both chambers are inflated to a similar pressure so that there is no inflation differential between them. The pad consequently exerts balanced radial forces on the circumference of the patella engaged thereby. The balanced radial forces maintain the patella in its natural position resistant to dislocation therefrom.

If the natural position of the patella is biomechanically incorrect, however, due to an injury or chronic condition, it is often desirable to reposition and retain the patella in a biomechanically corrected position rather than its natural position. Accordingly, the chambers are selectively inflated to different pressures creating an inflation differential between them. The pad consequently exerts unbalanced radial forces on the circumference of the patella engaged thereby as a function of the inflation differential. The unbalanced radial forces reposition the patella to the corrected position and resist dislocation therefrom.

The forces applied by the brace to the patella can be augmented by tightening one or more straps optionally provided along the sleeve against the patella in a desired configuration. Increasing or decreasing the tension of the straps correspondingly adjusts the level of force the strap applies to the patella. The strap tension is modified by repositioning the attachment points of the straps along the sleeve.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 1 is a conceptualized frontal view of a patella that is the treatment objective of the knee brace of the present invention.

FIG. 2 is a perspective view of a knee brace of the present invention in place on the leg of a user.

FIG. 3 is substantially the same view of the knee brace of FIG. 2, but having the anterior cover removed therefrom to show the position of the underlying pad on the sleeve.

FIG. 4 is a frontal view of the pad as employed in the knee brace of the present invention.

FIG. 5 is a cross-sectional plan view of the release valve of FIG. 4 as seen along line 5—5.

FIG. 6A is a cross-sectional view of the knee brace of FIG. 2 substantially as seen along line 6—6, wherein the brace applies balanced forces to the patella.

FIG. 6B is a cross-sectional view of the knee brace of FIG. 2 substantially as seen along line 6—6, wherein the brace applies unbalanced forces to the patella.

FIG. 7 is a perspective view of a knee brace of the present invention in place on the leg of a user with a full strap positioned on the sleeve to augment the forces applied to the patella.

FIG. 8 is substantially the same view of the knee brace of FIG. 7, but showing a half strap alternately positioned on the sleeve.

DESCRIPTION OF PREFERRED EMBODIMENTS

Referring initially to FIG. 1, a conceptualized patella 100 of the right knee joint is shown, the patella of the left knee joint being substantially identical. The patella 100 is the treatment objective of the knee brace of the present invention and, accordingly, is a frame of reference for the structure and utility of the present knee brace. The patella 100 is defined as having a patellar face 102 and a substantially triangular perimeter 104. The perimeter 104 is further defined to include four segments, i.e., medial and lateral sides 106, 108, a superior base 110 and an inferior apex 112. The medial and lateral sides and base 106, 108, 110 are substantially linear and the apex 112 is substantially arcuate.

Referring now to FIGS. 2 and 3, a knee brace of the present invention is shown and generally designated 10. The knee brace 10 is positioned on the right leg 12 of a user about the knee joint 14. The brace 10 comprises a sleeve 16 formed from a sheet of compliant material such as a natural or synthetic cloth, foam, elastomer, leather, or combination thereof. The sheet material is preferably relatively elastic as well as compliant, such that the sleeve 16 exerts a restorative force when stretched in substantially any direction. The preferred sheet material is a laminate of cloth-covered neoprene foam.

The sleeve 16 is typically fabricated by cutting one or more flat patterns from a planar sheet of the selected material and combining the pattern or patterns in a manner readily apparent to the skilled artisan to preform the sleeve 16 in the configuration of a tube. The tubular preformed sleeve 16 is mounted on the leg 12 by placing the foot 18 through the axial opening 20 of the sleeve and sliding the sleeve 16 up over the lower leg 22 until the sleeve 16 snugly encloses the knee joint 14. The sleeve 16 preferably has an anterior opening 24 formed therethrough that is positioned over the patella 100 exposing at least a portion of the patellar face 102. The restorative force of the elastic sheet material maintains the sleeve 16 in place about the knee joint 14.

Although not shown, the sleeve can alternatively be configured as a wrap having two free ends prior to mounting, rather than preformed as a tube. The wrap configuration of the sleeve is mounted on the leg by drawing the two free ends around the knee joint, joining the ends, and securing them with straps or the like, thereby transforming the wrap to a tube when mounted on the leg. This embodiment of the sleeve likewise falls within the scope of the present invention.

The brace 10 further comprises an anterior cover 26 fixedly attached along its perimeter to the anterior face 28 of the sleeve 16. The anterior cover 26 is fixed in place by attachment means such as stitching 30 to form a closed anterior pocket 32 between the posterior face of the anterior cover 26 and the anterior face 28 of the sleeve 16. The anterior cover 26 is preferably provided with an anterior opening 34 corresponding to the anterior opening 24 of the sleeve 16 which avoids covering the exposed portion of the patellar face 102. The profile of the anterior cover 26 corresponds substantially to the profile of a pad 36 enclosed within the anterior pocket 32 between the overlying anterior cover 26 and the underlying sleeve 16. A longitudinal partition 38 is placed in the anterior pocket 32 extending downwardly from the anterior opening 24 to facilitate proper positioning of the lower end 40 of the pad 36 within the anterior pocket 32. The longitudinal partition 38 is preferably stitching joining the anterior cover 26 and sleeve 16 along the length of the partition 38. The anterior cover 26 is formed from a sheet of compliant material that may be substantially the same material as the sheet material of the sleeve 16, but is preferably a material that is relatively inelastic or at least substantially less elastic than the sheet material of the sleeve 16. In addition, the material of the anterior cover 26 also preferably has the external character of either a hook coupling or a loop coupling of a hook and loop fastener pair commonly termed VELCRO. The material of the anterior cover 26 most preferably has the external character of a loop coupling. As such, the material of the anterior cover 26 can, for example, be a relatively inelastic weave of a synthetic cloth such as nylon or the like.

Medial and lateral covers 42a, 42b are fixedly attached along their perimeter to the medial and lateral faces 44a, 44b, respectively, of the sleeve 16. Like the anterior cover 26, the medial and lateral covers 42a, 42b are fixed in place by stitching 46a, 46b, respectively, to form closed medial and lateral pockets 48a, 48b, respectively, shown with reference to FIGS. 6A and 6B. The profiles of the medial and lateral covers 42a, 42b correspond substantially to the profiles of longitudinal stiffeners 50 enclosed within the medial and lateral pockets 48a, 48b. The stiffeners 50 are preferably formed from spiral metal stays and run longitudinally along substantially the entire length of the sleeve 16. Like the anterior cover 26, the medial and lateral covers 42a, 42b are also formed from a sheet of compliant material that may be substantially the same material as the sheet material of the sleeve 16, but is preferably a material that is relatively inelastic or at least substantially less elastic than the sheet material of the sleeve 16. The material of the medial and lateral covers 42a, 42b also preferably has the external character of either a hook coupling or a loop coupling, and most preferably of a loop coupling.

It is also noted with reference to FIG. 2 that a pair of manual valve actuators 52a, 52b, cooperatively functioning with the pad 36 as will be shown, protrude through the anterior cover 26 from the interior of the pocket 32. Details of the pad 36 and its cooperative elements are described hereafter with reference to FIGS. 4 and 5.

A preferred configuration of the pad 36 is described with specific reference to FIG. 4. The pad 36 is preferably formed from two continuous sheets of a film material. The film material is a highly-flexible, collapsible, fluid-impervious material. Materials exhibiting these characteristics include plastics, such as polyurethane, polyvinyl chloride, or the like. The pad 36 is constructed by overlaying one sheet atop the other and joining them together along their periphery using conventional means, such as r.f. welding, thereby forming a continuous peripheral seam 54 defining the outer perimeter of the pad 36 while maintaining a substantial void within the interior of the pad 36. The peripheral seam 54 outlines a substantially open-loop, horseshoe-shaped frontal profile of the pad 36 sized to circumscribe the anterior openings 24, 34 of the brace 10, and correspondingly the patellar perimeter 104, in their entirety with the exception of the inferior patellar apex 112 and lower portions of the anterior openings 24, 34. Accordingly, the pad 36 has a longitudinally-elongated, downwardly-tapered central opening 56 formed therethrough to receive the patella 100. The pad 36 further has a lower opening 58 formed through its lower end 40 to provide clearance for the inferior patellar apex 112 as well as the infrapatellar bursa and the patellar tendon (not shown) extending downwardly from the apex 112, thereby minimizing discomfort to a user of the brace 10.

The interior of the pad 36 bounded by the peripheral seam 54 is divided into two opposing fluid-tight pad chambers, a medial pad chamber 60a and a lateral pad chamber 60b. The medial and lateral pad chambers 60a, 60b are attached to each other at the upper end 61 of the pad 32 by means of a connective member 62 which is a continuation of the peripheral seam 54. The connective member 62 maintains the medial and lateral pad chambers 60a, 60b in fluid isolation from each other. The medial and lateral pad chambers 60a, 60b are configured as substantial mirror images of each other. Accordingly, the medial pad chamber 60a and elements associated therewith are described hereafter, as being representative of both pad chambers 60a, 60b and elements associated therewith. Medial elements are designated with the suffix "a", whereas corresponding lateral elements are designated with the suffix "b".

The medial pad chamber 60a has an elongated, arcuate, open-loop configuration corresponding to half of a horseshoe. Accordingly, the medial pad chamber 60a resembles an inverted "J" that substantially conforms to the entirety of the medial side 106 and a portion of the base 110 of the patella 100 which abut the medial pad chamber 60a across the intervening sleeve 16. In the manner of an inverted "J", the medial pad chamber 60a has a substantially linear elongated longitudinal segment 63a extending from the lower end 40 to the upper end 61 of the pad 36 in substantially corresponding alignment with the longitudinal axis of the sleeve 16. The longitudinal segment 63a is configured to abut the medial side 106 of the patella 100. Also in the manner of an inverted "J", the medial pad chamber 60a also has a shortened arcuate transverse segment 64a at the upper end 61 of the pad 36 that curves inwardly toward the opposing chamber 60b in substantially transverse alignment with the longitudinal axis of the sleeve 16.

A medial extension member 66a extends from the transverse segment 64a of the medial pad chamber 60a, having a manually operable medial release valve 68a, including the manual medial valve actuator 52a, mounted therein. A chamber port tube 70a extends between the interior of the medial extension member 66a and the interior of a medial pump chamber 72a associated with a medial pump 74a. The medial pump chamber 72a is a squeezable elastic bulb having good memory characteristics. The chamber port tube 70a has a passive one-way chamber valve 76a positioned on its lower end within the interior of the medial extension member 66a enabling selective fluid communication between the medial pad chamber 60a and the medial pump chamber 72a. The medial chamber valve 76a opens under sufficient fluid pressure in the direction of the medial pad chamber 60a, but is unresponsive to fluid pressure in the direction of the medial pump chamber 72a. Accordingly, the medial chamber valve 76a permits fluid flow exclusively in the direction of the medial pad chamber 60a from the medial pump chamber 72a.

In addition to the medial pump chamber 72a, the medial pump 74a comprises a pump port tube 78a extending from the interior of the medial pump chamber 72a out to the atmosphere. The pump port tube 78a has a passive one-way pump valve 80a positioned on its lower end within the interior of the medial pump chamber 72a enabling selective fluid communication between the medial pump chamber 72a and the atmosphere. The medial pump valve 80a is similarly configured to the medial chamber valve 76a to permit fluid flow exclusively in the direction of the medial pump chamber 72a from the atmosphere. Selective fluid communication between the medial pad chamber 60a and the atmosphere is provided by the medial release valve 68a described hereafter with reference to FIG. 5. The medial release valve 68a comprises the medial valve actuator 52a having a widened portion 82a at its lower end fitting into a valve seat 84a. The medial release valve 68a is maintained biased in a closed position by a spring 86a, but can be opened by manually depressing the valve actuator 52a against the force of the spring 86a.

The lateral pad chamber 60b, being a substantial mirror image of the medial chamber pad 60a, likewise has an elongated, arcuate, open-loop configuration corresponding to the half of the horseshoe opposing the medial pad chamber 60a. The lateral pad chamber 60b substantially conforms to the entirety of the lateral side 108 and a portion of the base 110 of the patella 100 which abut the lateral pad chamber 60b across the intervening sleeve 16. The lateral pad chamber 60b further has a substantially linear elongated longitudinal segment 63b and a shortened arcuate transverse segment 64b. A lateral extension member 66b extends from the transverse segment 64b of the lateral pad chamber 60b, having a manually operable lateral release valve 68b, including the manual lateral valve actuator 52b, mounted therein. A chamber port tube 70b extends from the interior of the lateral extension member 66b. Although a lateral pump is not shown in FIG. 4 in association with the lateral chamber 60b, it is understood that a lateral pump substantially identical to the medial pump 74a extends from the lateral extension member 66b.

It is noted that the medial and lateral pad chambers 60a, 60b are very large relative to the medial and lateral extension members 66a, 66b, respectively, insofar as the pad chambers 60a, 60b are the primary fluid reservoirs for the pad 36. The extension members 66a, 66b merely serve as flowpaths between the pad chambers 60a, 60b and their respective pumps 74a, 74b and release valves 68a, 68b. Accordingly, substantially all of the fluid capacity of the pad 36 is in the medial and lateral chambers 60a, 60b, which are both positioned in abutment with the patella 100 across the sleeve 16. No additional chambers or fluid reservoirs in continuous fluid communication with the medial and lateral pad chambers 60a, 60b are required for operation of the knee brace 10 as described hereafter.

METHOD OF OPERATION

Operation of the knee brace 10 is described with reference to FIGS. 6A, 6B, 7 and 8. Referring initially to FIGS. 6A and 6B, the brace 10 is shown in an operable position on the right leg 12 achieved by positioning the sleeve 16 over the knee joint 14 with a portion of the patellar face 102 exposed through the anterior opening 24 of the sleeve 16 and the patella 100 circumscribed by the pad 36 with the exception of the inferior apex 112. While positioning the sleeve 16 over the knee joint 14, the pad 36 is maintained substantially deflated. Once the sleeve 16 has been properly positioned, one or both of the pad chambers 60a, 60b are inflated with a fluid. The fluid can be a gas, liquid or gel, but is preferably a pneumatic fluid, and is most preferably ambient air.

The medial pad chamber 60a is inflated, for example, by taking air into the medial pump chamber 72a through the pump valve 80a and squeezing the pump chamber 72a to pump the air into the pad chamber 60a through the chamber valve 76a. As the medial pad chamber 60a inflates and expands, the relatively inelastic anterior cover 26 overlying the medial pad chamber 60a directs expansion of the pad chamber 60a in a radial direction having a substantially lateral component, thereby causing the medial pad chamber 60a to exert a corresponding radial force having a substantially lateral component against the medial side 106 of the patella 100. If it is desirable to adjust the fluid pressure of the medial pad chamber 60a, and consequently the radial force exerted thereby, fluid can be released from the pad chamber 60a through the medial release valve 68a by manually depressing the valve actuator 52a.

It is apparent from the above, that the lateral pad chamber 60b can be similarly inflated or deflated to exert an adjustable radial force having a substantially medial component against the lateral side 108 of the patella 100.

Referring specifically to FIG. 6A, both pad chambers 60a, 60b are shown inflated to an equal fluid pressure such that no fluid pressure differential exists between them. When both chambers 60a, 60b are inflated equally, as shown here, the radial forces exerted by the two chambers 60a, 60b on the medial and lateral sides 106, 108 of the patella 100 are balanced. Consequently, this balanced mode of operation is selected when it is desired to securely retain the patella 100 in its inherently natural position resistant to dislocation therefrom.

Referring to FIG. 6B, the medial pad chamber 60a is shown inflated to a fluid pressure substantially greater than the fluid pressure of the lateral pad chamber 60b such that a substantial pressure differential exists between them. The medial pad chamber 60a correspondingly exerts a greater radial force on the medial side 106 of the patella 100, than the opposing radial force exerted by lateral chamber pad 60b on the lateral side 108 of the patella 100. Accordingly, the medial pad chamber 60a dislocates the patella 100 in a substantially lateral direction. This unbalanced mode of operation is selected when it is desired to correct the natural position of the patella 100 by repositioning and retaining the patella 100 in a biomechanically corrected position.

It is apparent that the lateral pad chamber 60b can similarly be inflated to a substantially greater fluid pressure than the medial pad chamber 60a, if it is alternatively desired to dislocate the patella 100 in a substantially medial direction. It is further apparent that the degree of patellar dislocation in the lateral or medial direction can be selectively adjusted by adjusting the pressure differential between the medial and lateral pad chambers 60a, 60b.

Augmentation of the forces applied by the chamber pads 60a, 60b to the patella 100 is provided by positioning one or more straps along the sleeve 16 during either the balanced or unbalanced mode of operation. FIG. 7 shows one embodiment of a strap configuration wherein a single full strap 88 extends circumferentially around the patella 100 and sleeve 16. The strap 88 is provided with an attachment means along its length (not shown) such as a VELCRO coupling, preferably a hook coupling, which enables attachment of the strap 88 to the anterior, medial or lateral covers 26, 42a, 42b on the sleeve 16 at any number of positions. As shown, the full strap 88 is positioned over the upper end 61 of the pad 36 at a selected tension, thereby applying a substantially orthogonal force along the entire length of the patellar base 110 that is directed inward relative to the knee joint 14. The orthogonal force effectively tilts the entire patellar base 110 inward as desired by the user. Increasing the tension of the strap 88 by drawing it tighter and reattaching it to the sleeve 16, increases the orthogonal force on the patellar base 110, thereby effectively increasing the inward tilt of the patellar base 110. It is apparent that the strap 88 can be similarly placed over the lower end 40 of the pad 32 to tilt the patellar apex 112 inward.

FIG. 8 shows another embodiment of a strap configuration wherein a single half strap 90 extends circumferentially around substantially half of the patella 100 and sleeve 16. Like the full strap 88, the half strap 90 is provided with an attachment means along its length (not shown) such as a VELCRO coupling, preferably a hook coupling, which enables attachment of the strap 90 to the anterior, medial or lateral covers 26, 42a, 42b on the sleeve 16 at any number of positions. As shown, the half strap 90 is positioned over only the medial transverse segment 64a of the pad 36 at a selected tension, thereby applying a substantially orthogonal force along the patellar base 110 to only the upper medial quadrant of the patella 100. The orthogonal force is directed inward relative to the knee joint 14, effectively tilting the upper medial quadrant of patella 100 inward as desired by the user. Increasing the tension of the strap 90 by drawing it tighter and reattaching it to the sleeve 16, increases the orthogonal force on the upper medial quadrant of the patella 100, thereby effectively increasing the inward tilt thereof. It is apparent that the strap 90 can be similarly placed over the upper lateral, lower medial or lower lateral quadrants to tilt them inward as desired.

Although the knee brace of the present invention and its method of operation have been described above as applied to the right leg, it is apparent to the skilled artisan that the brace is readily adaptable for application to the left leg. Furthermore, in the preferred embodiment of the pad 36, as described above, each pad chamber 60a, 60b is provided with a separate pump 74a, 74b and release valve 68a, 68b. It is apparent, however, to the skilled artisan that within the scope of the present invention a single pump and release valve can be configured to individually service both pad chambers 60a, 60b. The pad chambers 60a, 60b are also described above as being attached to each other by the connective member 62. It is further apparent to the skilled artisan that within the scope of the present invention the connective member 62 can be eliminated, thereby physically separating the pad chambers 60a, 60b without altering the function of the pad 36. Finally, it is apparent to the skilled artisan that within the scope of the present invention, either one of the pad chambers 60a, 60b can be eliminated from the brace and the brace can effectively operate with a single pad chamber 60a or 60b, thereby applying a radial force to the patella in only one direction in accordance with an unbalanced mode of operation.

While the particular knee brace shown and disclosed herein is fully capable of obtaining the objects and providing the advantages stated herein, it is understood that this brace is merely illustrative of a presently preferred embodiment of the invention and that other embodiments are possible within the scope of the present invention.

We claim:

1. A knee brace mountable on a leg of a user about a knee joint which includes a patella having a base, an apex, a medial side and a lateral side, said knee brace comprising:

a compliant sleeve positionable over the knee joint, said sleeve having an anterior face and a longitudinal axis alignable with the longitudinal axis of the knee joint;

a substantially H-shaped hollow fluid-inflatable pad having a lateral side and a medial side joined by a cross bar, each side comprising a distal leg and a proximal arm, said pad disposed on the anterior face of said sleeve, alignable with said longitudinal axis of the knee joint, and positionable about said patella such that said legs lie respectively closely laterally of said lateral side and closely medially of said medial side of said patella and said cross bar lies closely proximal of said apex of said patella;

a fluid-tight barrier disposed across the interior of said hollow cross bar dividing said pad into lateral and medial hollow chambers, each chamber comprising the hollow interior of the respective side of said pad and of the adjacent portion of said cross bar;

the distal ends of said legs sized and configured to extend distally of said base of the patella and to curve toward each other distally of the patella but remaining spaced apart from each other when the brace is positioned properly in use;

fluid pump means exteriorly of said pad and in selective separate fluid communication with the hollow interiors of said arms of said lateral and medial chambers for inflation thereof;

lateral and medial valve means incorporated respectively into said lateral and medial chambers and providing fluid communication between said hollow interiors thereof and the exterior of said pad for deflation thereof; and cover means overlying said pad anteriorly of said sleeve and securable to said anterior face of said sleeve, said sleeve and said cover secured thereto cooperating to maintain said pad disposed in said position with respect to said patella, such that said pad operates to apply directional pressure against said patella in accordance with the degree of inflation of each said chamber.

2. A knee brace as recited in claim 1, wherein said lateral and medial chambers constitute substantially the entire fluid capacity of said pad.

3. A knee brace as recited in claim 1 further comprising at least one strap adjustably disposed in a substantially circumferential position on said sleeve.

4. A knee brace as recited in claim 3 wherein said strap is positioned with respect to said patella such that tightening of said strap about said user's leg augments the pressure of said chambers against said patella.

5. A knee brace as recited in claim 1, wherein said sleeve is formed from first elastic material.

6. A knee brace as recited in claim 5, wherein said anterior cover is formed from a second material which is relatively less elastic than said first material.

7. A knee brace as recited in claim 6 wherein said second material comprising said cover is sufficiently less elastic than said first material comprising said sleeve that expansion of said pad by inflation of either of said chambers is resisted by said cover and the pad during expansion is urged by the resistant cover posteriorly toward said knee joint.

8. A knee brace as recited in claim 1, wherein an anterior opening is formed through said anterior face of said sleeve.

9. A knee brace as recited in claim 1 wherein said pump means comprises a single pump providing selective fluid communication between the exterior of said pad and, alternatively, the hollow interior of said lateral chamber and the hollow interior of said medial chamber.

10. A knee brace as recited in claim 1 wherein said pump means comprises a first pump providing selective fluid communication between the hollow interior of said lateral chamber and the exterior of said pad and a second pump providing selective fluid communication between the hollow interior of said medial chamber and the exterior of said pad.

11. A knee brace as recited in claim 1 wherein said pump means is releaseably attached in fluid communication with said chambers.

12. A knee brace as recited in claim 11 further comprising sealing valve means for interrupting said fluid communication when said pump means is removed from fluid communication with said chambers and preventing release of fluid present in said chambers.

13. A knee brace as recited in claim 1 wherein said chambers are pressurized substantially equally and said directional pressure is exerted generally equally around the circumference of said patella, such that said patella is maintained in its normal position.

14. A knee brace as recited in claim 1 wherein said chambers are pressurized substantially unequally and said directional pressure is exerted generally unequally around the circumference of said patella, such that said patella is urged from an abnormal position toward its normal position.

15. A knee brace as recited in claim 4 comprising a plurality of said straps, each of which augments said pressure against said patella from a different direction.

16. A knee brace as recited in claim 1 further comprising at least one stiffening member disposed longitudinally of said brace and affixed to the lateral or medial side of said sleeve.

17. A knee brace as recited in claim 16 further comprising two stiffening members each disposed longitudinally of said brace and affixed, respectively, to the lateral and medial sides of said sleeve.

18. A knee brace as recited in claim 16 further comprising at least one strap adjustably disposed in a substantially circumferential position on said sleeve and abutting the external side of said stiffening member, such that tensioning of said strap urges said stiffening member toward said knee joint.

* * * * *